US010219939B1

(12) United States Patent
Bashir

(10) Patent No.: US 10,219,939 B1
(45) Date of Patent: Mar. 5, 2019

(54) SURGICAL OPHTHALMIC INTRA OCULAR ACCESS TOOL

(71) Applicant: Samer Jaber Bashir, Manama (BH)

(72) Inventor: Samer Jaber Bashir, Manama (BH)

(*) Notice: Subject to any disclaimer, the term of this patent is extended or adjusted under 35 U.S.C. 154(b) by 0 days.

(21) Appl. No.: 16/136,614

(22) Filed: Sep. 20, 2018

Related U.S. Application Data

(60) Provisional application No. 62/572,423, filed on Oct. 14, 2017.

(51) Int. Cl.
| | | |
|---|---|---|
| *A61F 9/00* | (2006.01) | |
| *A61F 9/007* | (2006.01) | |
| *A61F 2/16* | (2006.01) | |
| *A61F 9/008* | (2006.01) | |
| *A61F 9/013* | (2006.01) | |

(52) U.S. Cl.
CPC ...... *A61F 9/00736* (2013.01); *A61F 9/00781* (2013.01); *A61B 2217/005* (2013.01); *A61F 2/1662* (2013.01); *A61F 9/008* (2013.01); *A61F 9/013* (2013.01)

(58) Field of Classification Search
CPC ............ A61F 9/00736; A61F 9/00781; A61F 2/1662; A61F 9/008; A61F 9/013; A61B 2217/005
USPC ........................................................ 606/130
See application file for complete search history.

(56) References Cited

U.S. PATENT DOCUMENTS

| | | | | |
|---|---|---|---|---|
| 4,688,570 A | * | 8/1987 | Kramer ................... | A61F 9/013 606/166 |
| 5,624,456 A | * | 4/1997 | Hellenkamp ........... | A61F 9/013 606/166 |
| 5,772,675 A | * | 6/1998 | Hellenkamp ........... | A61F 9/009 606/166 |
| 5,807,380 A | * | 9/1998 | Dishler ................ | A61F 9/00802 606/166 |
| 5,876,415 A | * | 3/1999 | Pierce ..................... | A61F 9/013 606/166 |
| 5,980,543 A | * | 11/1999 | Carriazo ................. | A61F 9/013 606/166 |
| 6,007,553 A | * | 12/1999 | Hellenkamp ........... | A61F 9/013 606/166 |
| 6,090,119 A | * | 7/2000 | Pierce ..................... | A61F 9/013 604/22 |
| 6,258,110 B1 | * | 7/2001 | Hellenkamp ........... | A61F 9/013 606/166 |

(Continued)

*Primary Examiner* — Amy R Weisberg

(57) ABSTRACT

A surgical ophthalmic intra ocular access tool comprising a platform having a walled structure with central space(s), that is placed on the surface of the eye; a set or more of track(s) with entry and exit port(s) travelling within the wall(s) at a certain angle and length; a needle hub receiver(s) that allows universal attachment of any injecting device(s) with an opening to the bottom of the surgical ophthalmic intra ocular access tool; a projecting marker(s) on one or more sides; a set of repeated projections from the underside of the surgical ophthalmic intra ocular access tool to facilitate gripping to the eye tissue underneath; a rail like system outlining the inner as well as the outer walls, allowing multiple accessory(s) to be attached to either rail to facilitate surgical intervention(s) and predesigned holes at lower edge of said surgical ophthalmic intra ocular access tool in contact with eye wall(s) allowing for suturing in order to obtain secure attachment(s) or augmented wall(s) support.

7 Claims, 14 Drawing Sheets

(56) References Cited

U.S. PATENT DOCUMENTS

| | | | | |
|---|---|---|---|---|
| 6,312,403 | B1* | 11/2001 | Ruiz | A61F 9/007 604/23 |
| 7,166,117 | B2* | 1/2007 | Hellenkamp | A61F 9/013 606/166 |
| 7,780,689 | B2* | 8/2010 | Barrile-Josephson | A61F 9/013 606/166 |
| 7,824,372 | B1* | 11/2010 | Kurup | A61F 9/0017 604/116 |
| 9,144,516 | B2* | 9/2015 | Goncalves | A61F 9/0017 |
| 9,445,942 | B2* | 9/2016 | Futamura | A61F 9/00736 |
| 9,681,981 | B2* | 6/2017 | Stevens | A61F 2/16 |
| 2003/0078607 | A1* | 4/2003 | Carriazo | A61F 9/013 606/166 |
| 2003/0220653 | A1* | 11/2003 | Perez | A61F 2/142 606/107 |
| 2004/0002722 | A1* | 1/2004 | Slade | A61F 9/013 606/166 |
| 2004/0147944 | A1* | 7/2004 | LaHaye | A61F 9/009 606/166 |
| 2005/0288697 | A1* | 12/2005 | Tei | A61B 17/3403 606/166 |
| 2007/0244496 | A1* | 10/2007 | Hellenkamp | A61F 9/013 606/166 |
| 2011/0022035 | A1* | 1/2011 | Porter | A61F 9/00825 606/4 |
| 2014/0276673 | A1* | 9/2014 | Heitel | A61F 9/009 606/4 |
| 2017/0348148 | A1* | 12/2017 | Bigler | A61F 9/00781 |
| 2017/0348151 | A1* | 12/2017 | Ahmed | A61F 9/00781 |
| 2018/0228568 | A1* | 8/2018 | Kato | A61B 90/11 |
| 2018/0311075 | A1* | 11/2018 | Camras | A61F 9/00781 |

\* cited by examiner

SURGICAL OPHTHALMIC INTRA OCULAR ACCESS TOOL

CROSS-REFERENCE TO RELATED APPLICATIONS

The present application claims priority to U.S. provisional patent application Ser. No. 62/572,423, filed on Oct. 14, 2017. The entire disclosure is included herein in its entirety at least by reference.

BACKGROUND OF THE INVENTION

1. Copyright Notice

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Field of the Invention

The present disclosure relates to medical and surgical ophthalmological tools.

3. Discussion of the Related Art

Millions of eyeball surgeries occur daily around the world to inject a substance e.g. medicine or withdraw contents from inside, remove and/or modify diseased tissues and/or implant new devices to induce healing and promote health. Such access is obtained without any standardization and varies greatly depending upon experience and training of personnel.

The usual way of gaining surgical access to the inside of the eye has high damage potential to the eye or complicating a simple task.

The current practice is to open the eye with a device called speculum to spread the eyelids exposing most of the front of the eye. Then a measuring device similar to a miniature ruler called caliper is applied from the corneal limbus (junction of cornea and sclera) to a set distance of the operator choosing. Then the surgical incision(s) is initiated at a variable angle and penetration without any standardization. Age of the patient, status of the eye and movement of the patient eyes are variables, which could and does lead to complications affecting the health of the eye intended to be treated. The skill and experience of the operator are also variables causing high risk. There is not a single device to serve as a safe standard for gaining access, which is skill, training, age, species and anatomical variation dependent.

The only prior art is very limited in design, application and scope with only one specified entry port at 3.5 mm from the limbus. U.S. Pat. No. 9,144,516 B2 claims facilitating administration only (not obtaining) through a single entry port for injection set only at 3.5 mm. The device provides no claim for intraocular access including but not limited to withdrawal in the form of taking sample(s) for testing or to alter the content(s) and/or pressure of the eyeball. It also does not claim varying distances or angles to the said procedure. The said device also does not support adjustability to various eye conditions in different ages. This can range from premature babies to children to full-grown adults with different intraocular lens conditions ranging from Aphakia (no lens neither natural nor artificial inside the eye), Phakia (Natural lens is still in its place inside the patient's eye) or even in cases of pseudophakia (Artificial implanted lens inside the eye). This said prior art also does not claim any surgical support and/or application.

All of these disadvantages work together to affect general wellbeing of eyes through many variables resulting in many complications seen daily at various health care facilities. Therefore, the need exists in the field of diagnostic, therapeutic and surgical eye care in humans as well as animals, for a standardized access-granting tool to the contents of the eye in any age group. Such tool is desperately missing and our invention provides the answer. The present invention provides such a method and the overall combination of these features is nowhere disclosed in the prior art cited above which appears to be representative of the general art in this area although it is not intended to be an all-inclusive listing of pertinent prior art patents.

SUMMARY OF THE INVENTION

In light of the disadvantages of the prior art, the following summary is provided to facilitate an understanding of some of the innovative features unique to the present invention and is not intended to be a full description. A full appreciation of the various aspects of the invention can be gained by taking the entire specification, claims, drawings, and abstract as a whole.

The present invention seeks to provide a solution to these problems by providing a surgical multipurpose device and/or a platform for standardizing intraocular access for injecting, implanting, modifying, removing and/or obtaining substance(s), tissue(s), content(s), medicine(s), or sample(s) from a human eye(s) or an animal eye(s), in any age group(s), once the device is fixed and/or attached to front of the eye.

Preferably, in one embodiment of the present invention, a set guidance track(s) with entry and exit port(s) is pre designed to provide specific distance(s) and angle(s), facilitating and granting access for injecting, implanting, modifying, removing and/or obtaining substance(s), tissue(s), content(s), medicine(s), or sample(s) from a human eye(s) or an animal eye(s), in any age group(s).

Preferably, in another embodiment of the present invention, a set space(s) is pre designed centrally to provide a rail base for different matching accessories that are specifically pre-designed to suit different surgical application(s) including but not limited to anterior segment surgeries.

Preferably, in yet another embodiment of the present invention, a predesigned rail system that runs at the outer walls of the said device. A rail attachment accessory(s) is specifically predesigned to suit different surgical applications including but not limited to posterior segment surgeries.

Preferably, in another embodiment of the present invention, an adapter is pre designed to provide manual, automatic, electric or remote surgical manipulations of different surgical instruments once inserted through the surgical platform either to the outside or inside of the eyeball depending upon surgical maneuvers.

This Summary is provided merely for purposes of summarizing some example embodiments, so as to provide a basic understanding of some aspects of the subject matter described herein.

Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE DRAWING FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments. These accompanying drawings, by way of example only and in no way limiting the scope of the invention, in which:

Figure 1:
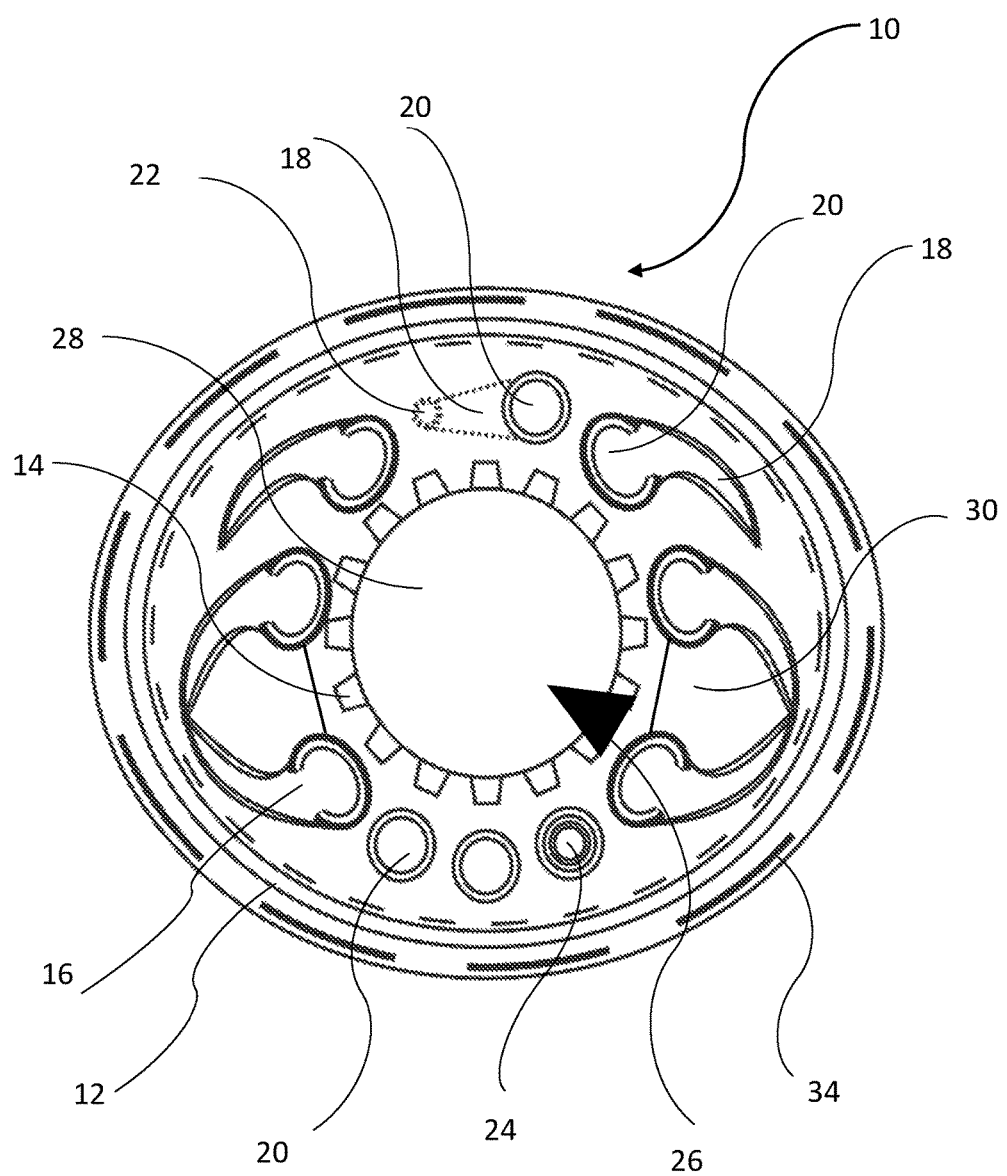
FIG. 1 shows an elevation view from the top of the device according to an embodiment of the present invention.
Figure 2:
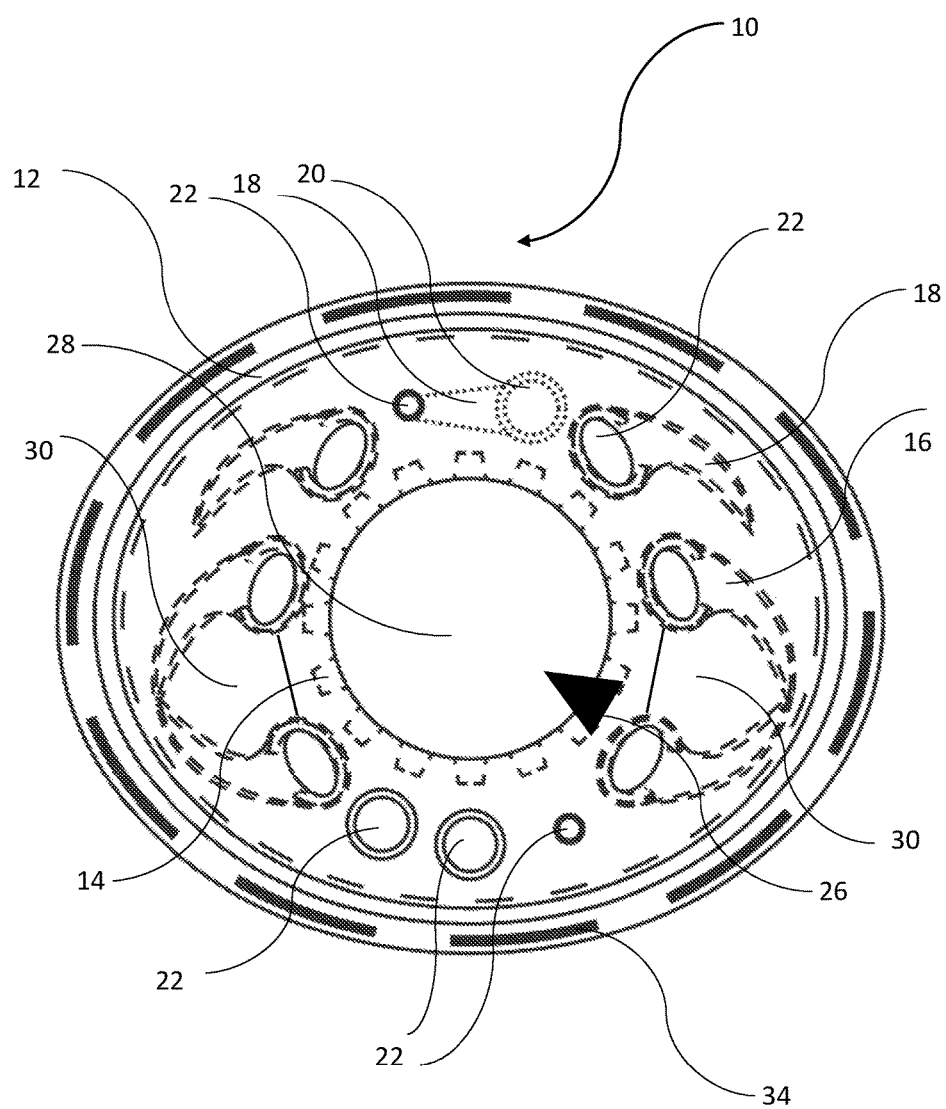
FIG. 2 shows an elevation view from the bottom of the device in FIG. 1.
Figure 3:
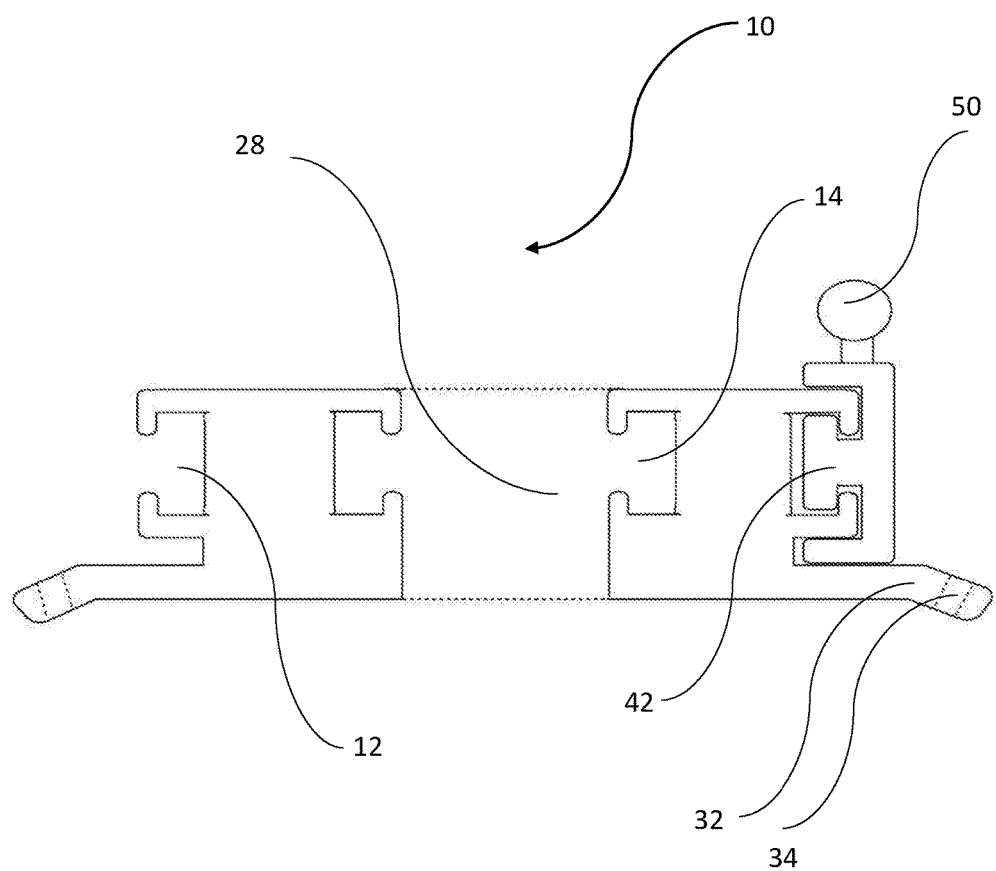
FIG. 3 shows a section view from front to back of the device of FIG. 1 with an accessory attached to outer rail system.
Figure 4:
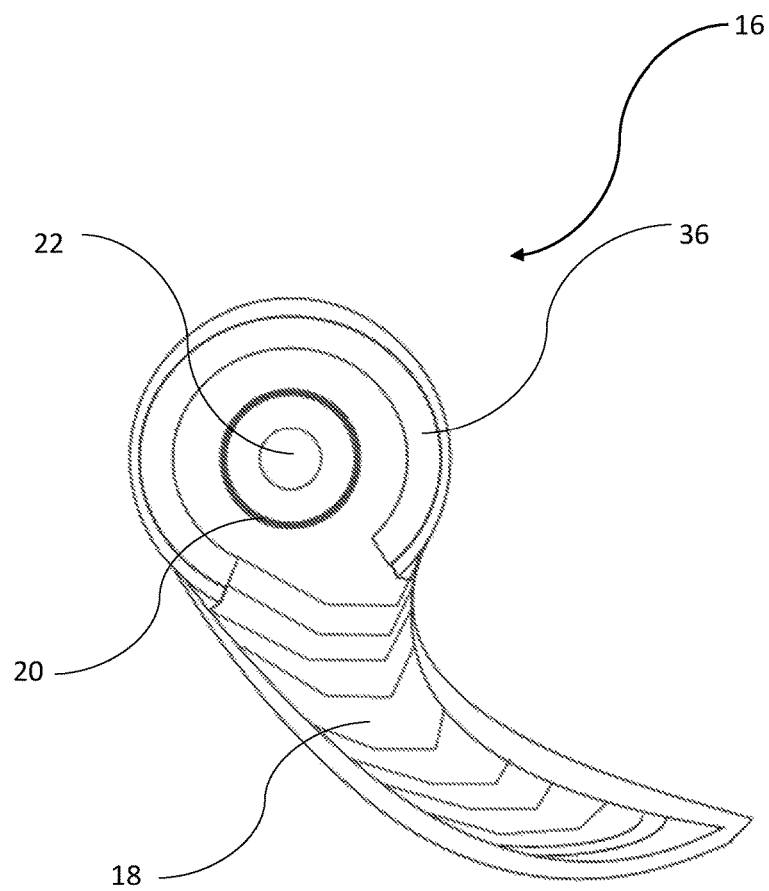
FIG. 4 shows an elevation view from the top of the port system as part of device in FIG. 1.
Figure 5:
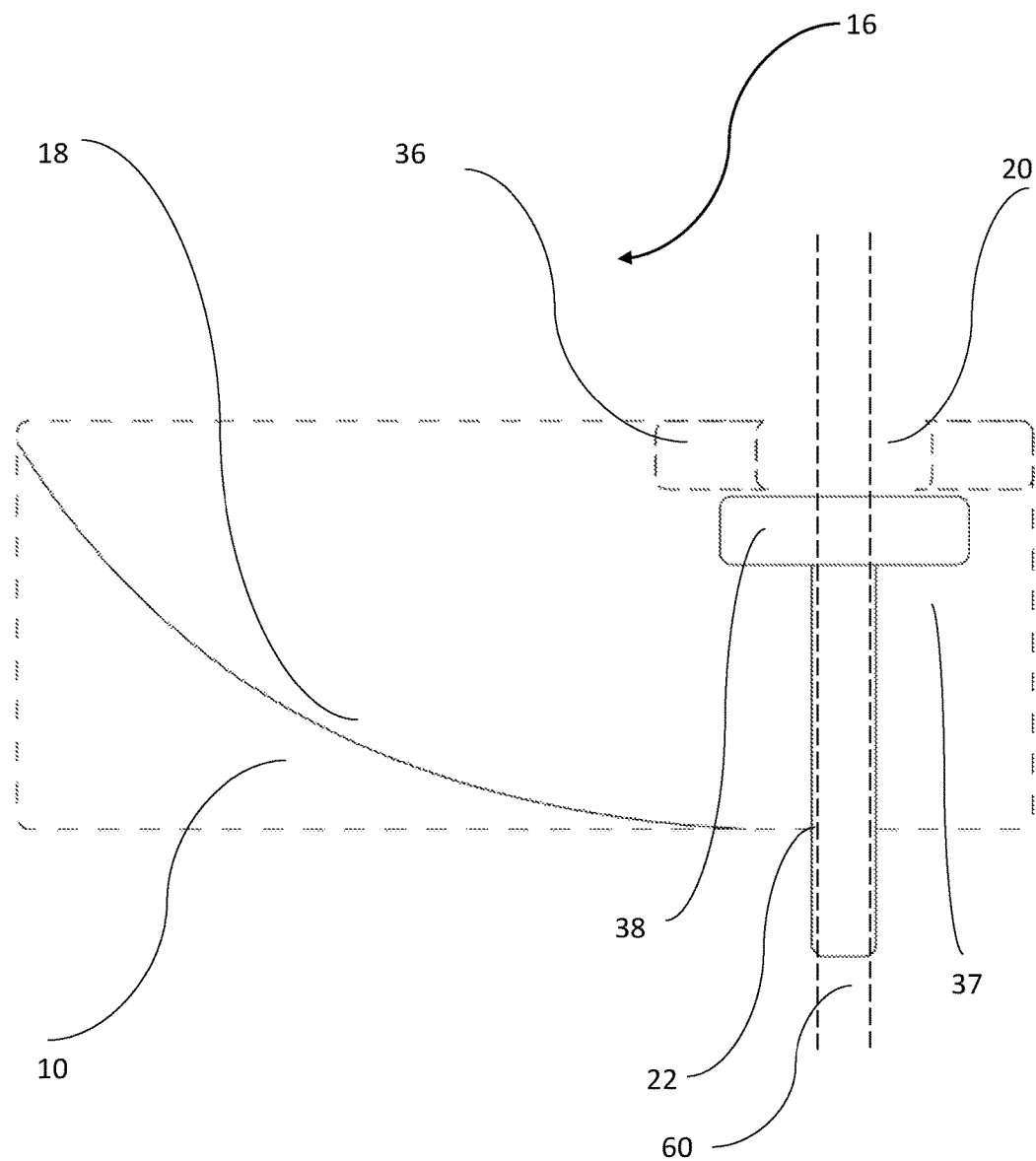
FIG. 5 shows a section view from one side of the device of FIG. 4.
Figure 6:
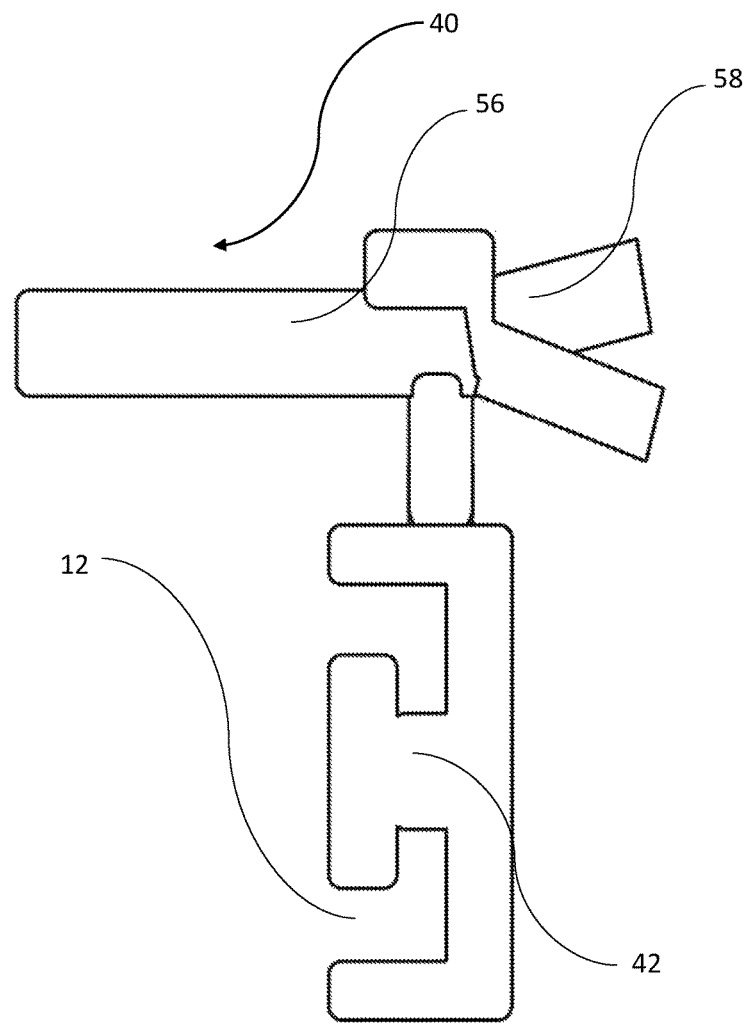
FIG. 6 shows an elevation view from one side of the microcontroller accessory according to an embodiment of the present invention.
Figure 7:
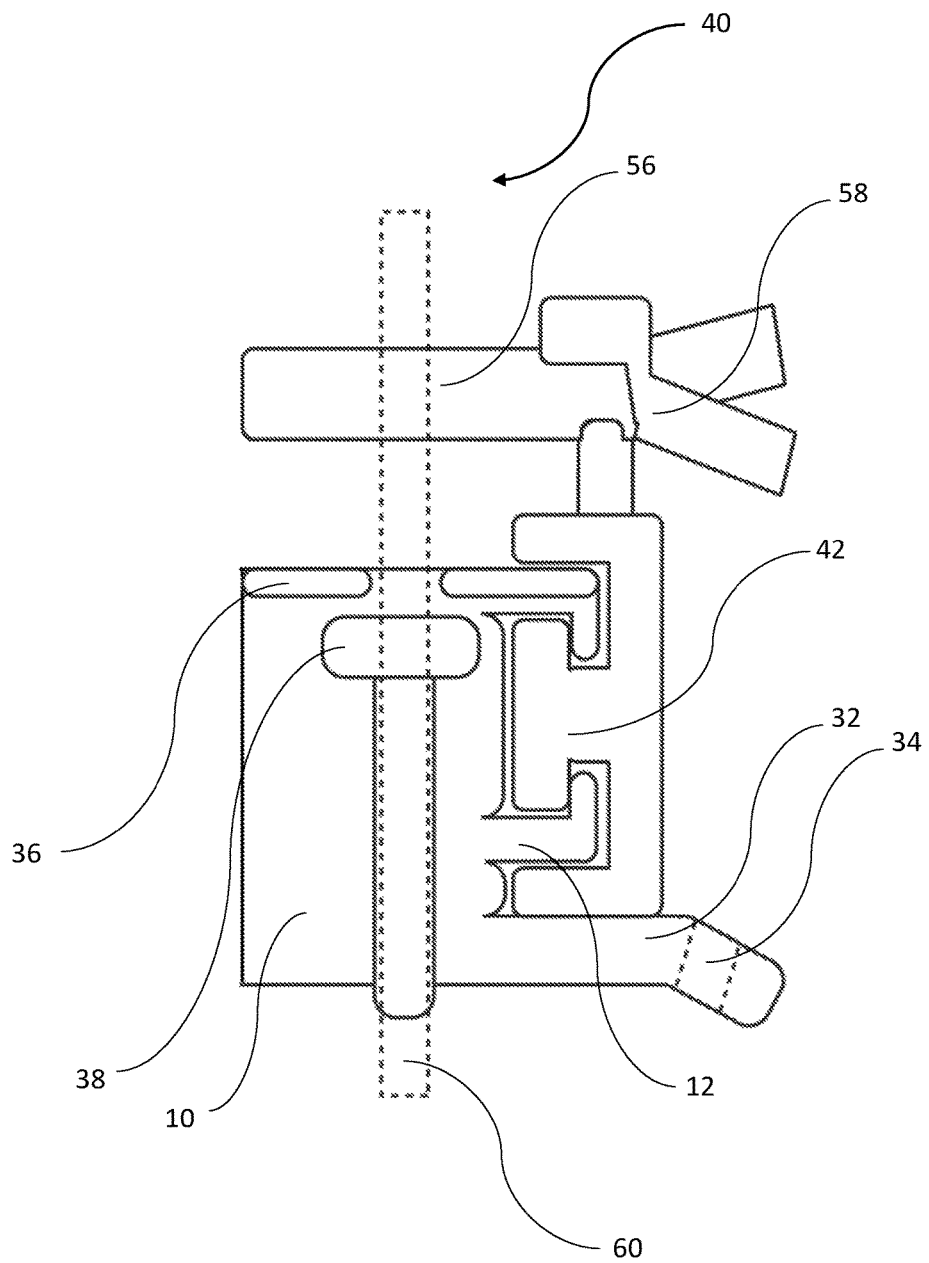
FIG. 7 shows a section view from one side of the microcontroller attached to a rail system of the device of FIG. 6.
Figure 8A:
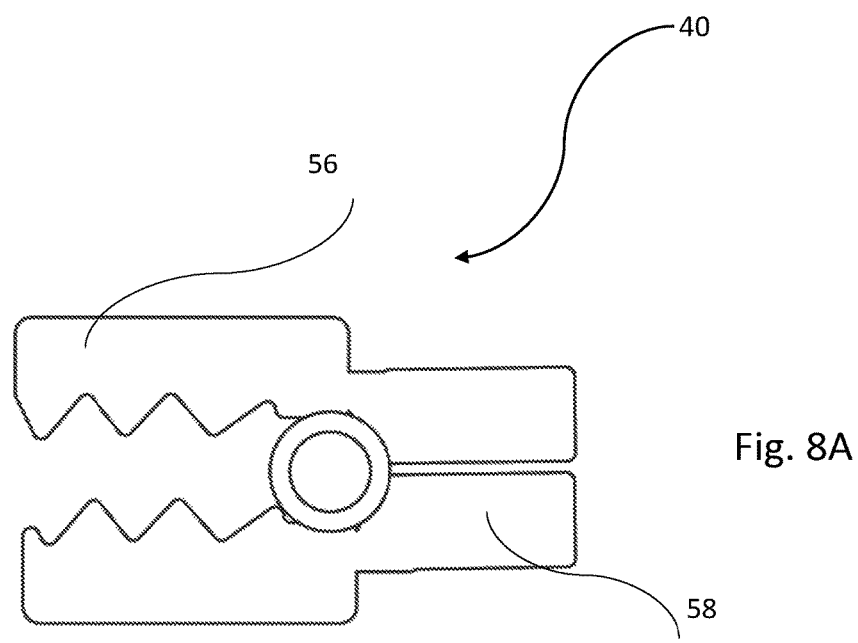
FIG. 8A shows an elevation view from the top of clamp system according to an embodiment of the present invention showing an open status.
Figure 8B:
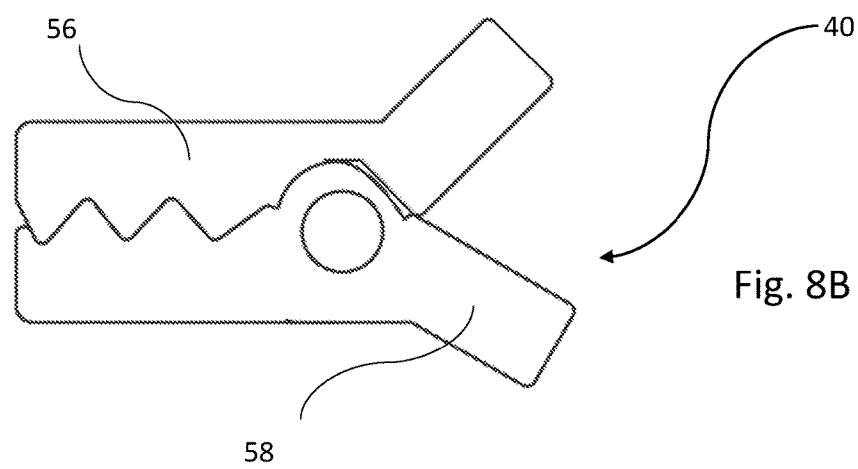
FIG. 8B shows an elevation view from the top of clamp system according to an embodiment of the present invention showing a closed status.
Figure 9:
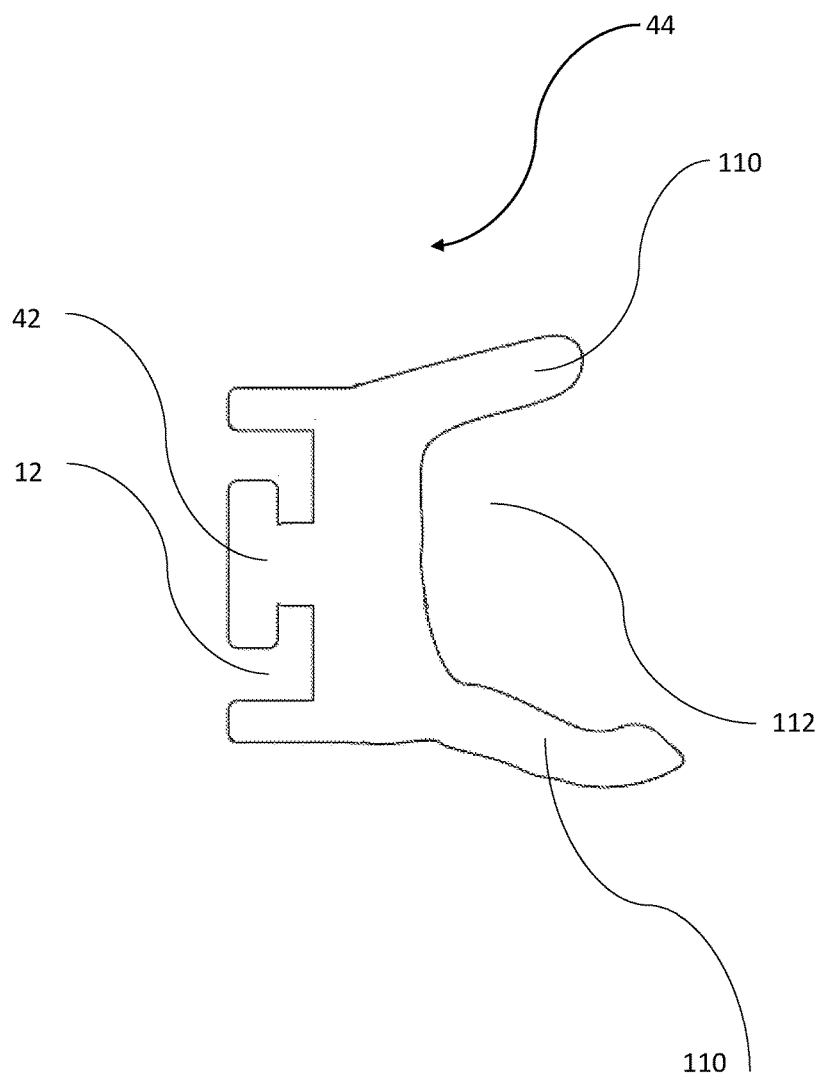
FIG. 9 shows a section view from the side of eyelid speculum accessory according to an embodiment of the present invention.
Figure 10A:
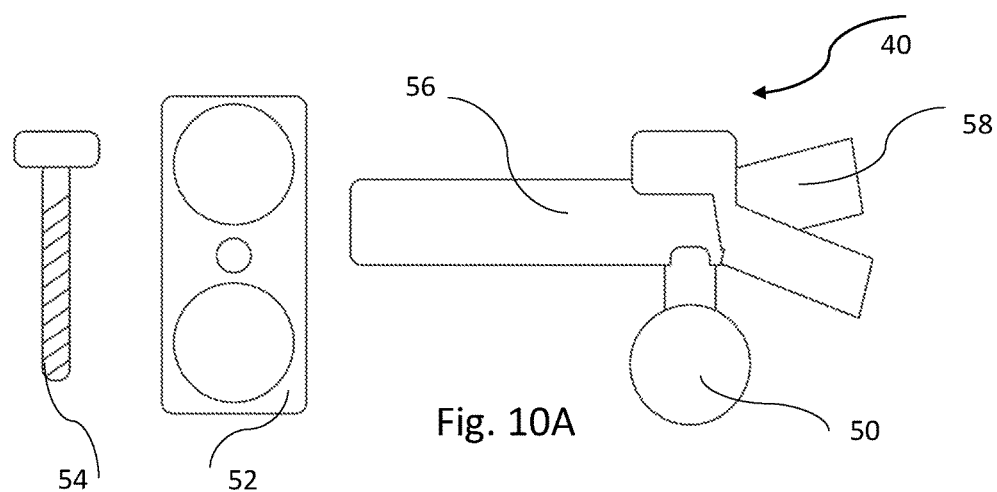
FIG. 10A shows a first section schematic view of a two-stage microcontroller assembly to attach to the rail system of the device in FIG. 1.
Figure 10B:
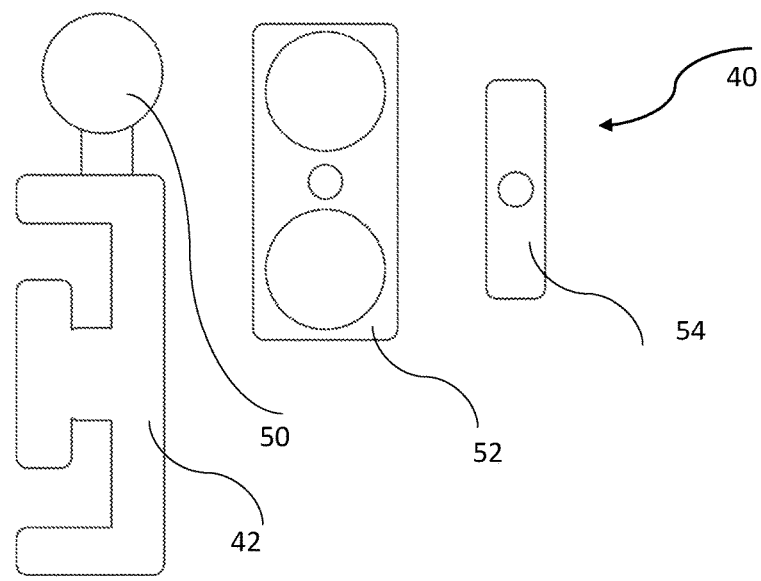
FIG. 10B shows a second section schematic view of a two-stage microcontroller assembly to attach to the rail system of the device in FIG. 1.
Figure 11:
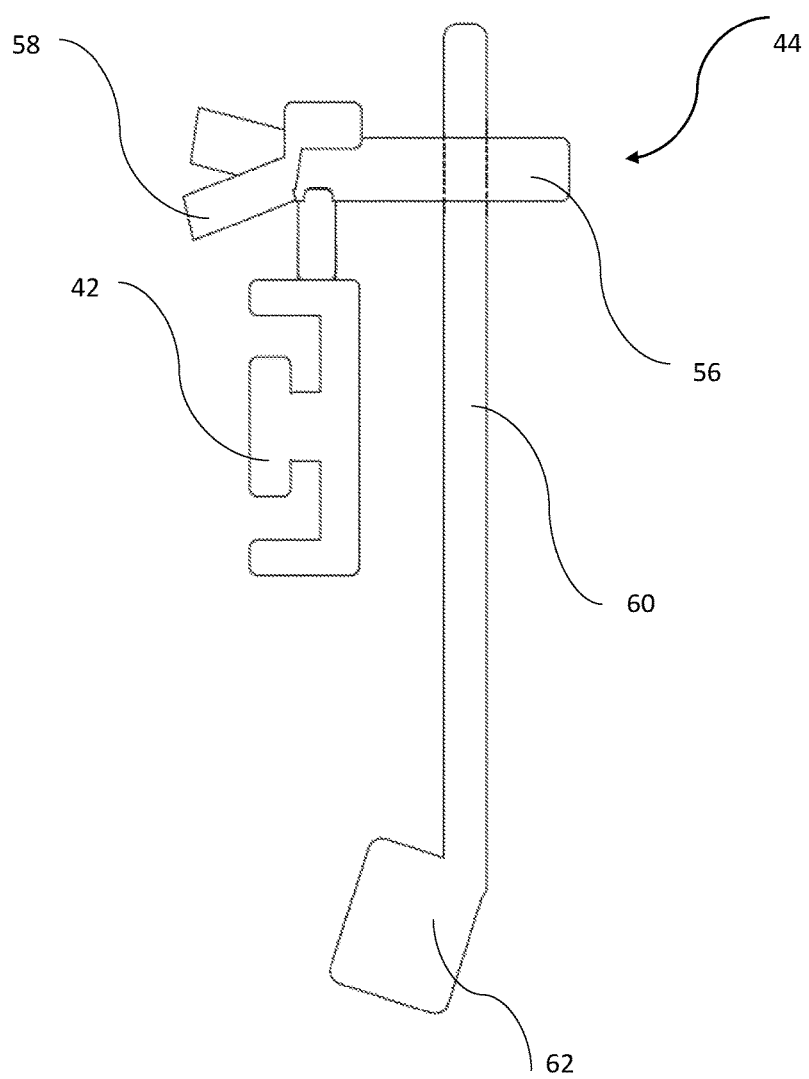
FIG. 11 shows an elevation view from the side of an indenter accessory to attach to the rail system of the device in FIG. 1 according to an embodiment of the present invention.
Figure 12:
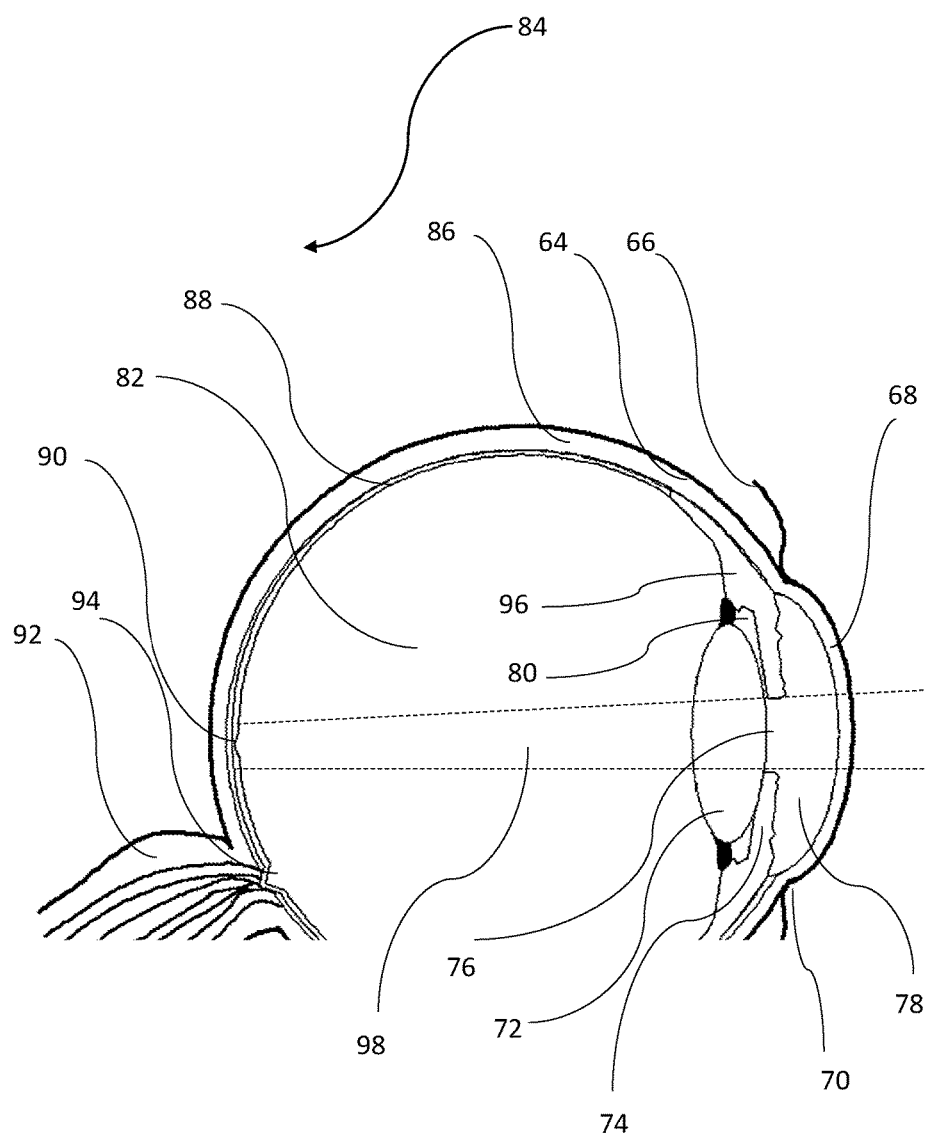
FIG. 12 shows a section view of an eye to highlight anatomical structures.
Figure 13:
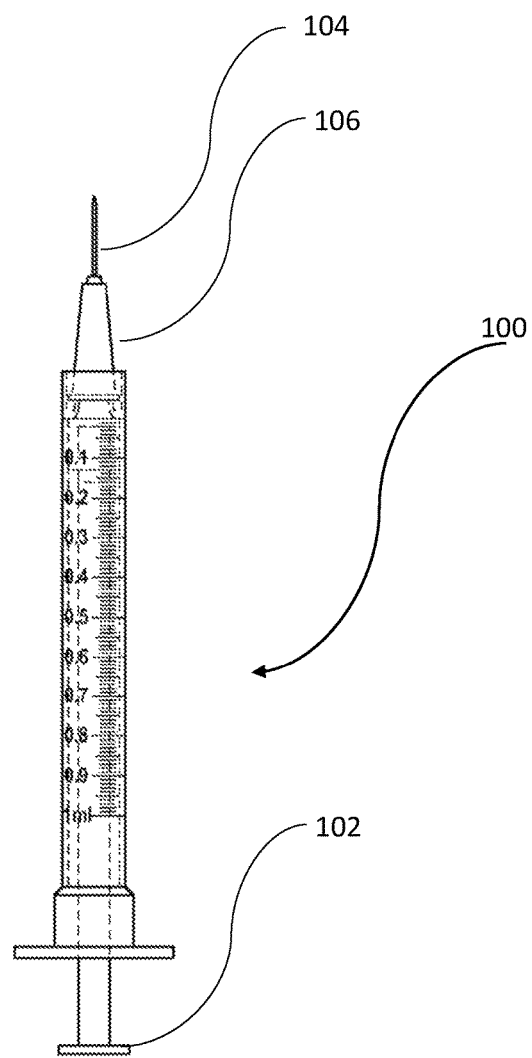
FIG. 13 shows a schematic of a conventional syringe with its parts explained (Prior Art).
Figure 14:
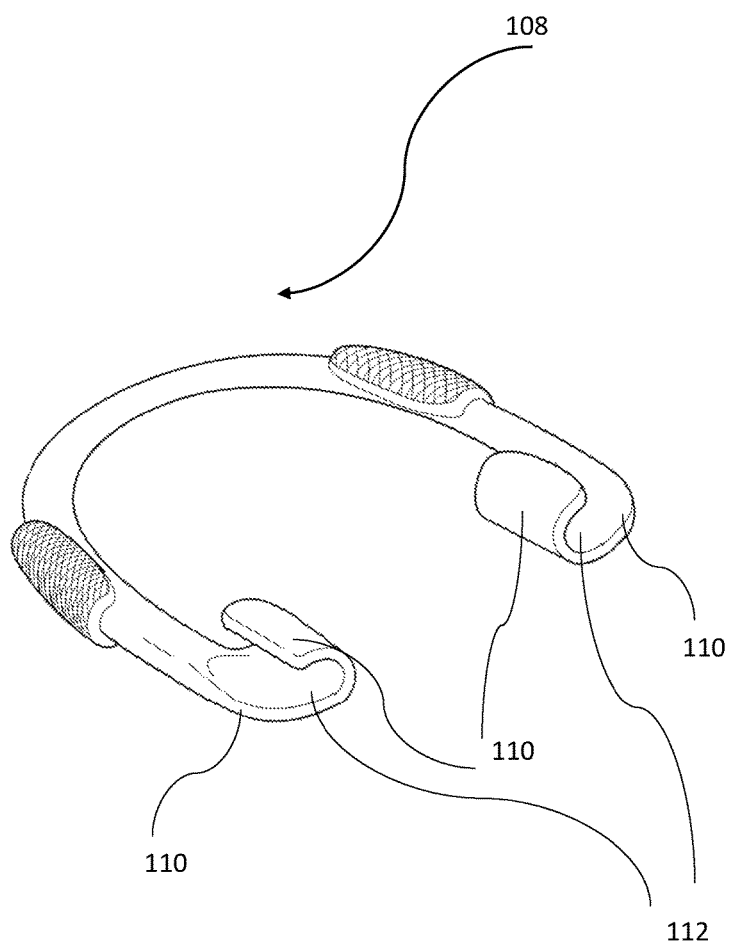
FIG. 14 shows a schematic of a conventional speculum with its parts explained (Prior Art).

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Before explaining the invention in detail, it is to be understood that the invention is not limited in its application to the detail of application illustrated in the drawings since the invention is capable of other embodiments and of being practiced or carried out in various ways. It is also to be understood that the phraseology or terminology employed is for the purpose of description only and not of limitation. The present invention is described in enabling detail in the following examples, which may represent more than one embodiment of the present invention.

In use, a surgical ophthalmic intra ocular access tool 10 for standardizing intraocular surgical access for injecting, implanting, modifying, removing and/or obtaining substance(s), tissue(s), content(s), object(s), medicine(s), or sample(s) from a human eye(s) or an animal eye(s) 84, in any age group(s), once the surgical ophthalmic intra ocular access tool 10 is fixed and/or attached to front of the eye 84.

The surgical ophthalmic intra ocular access tool 10 also simplifies the procedure(s) by eliminating at least two more tools; an eyelid opening and separating tool called "Speculum" 108 and a measuring device called "Caliper" that were complicating the usual procedure(s).

The surgical ophthalmic intra ocular access tool 10 can be for a single use (disposable) or for multiple uses (reusable) after industry-standard protocols of disinfection are properly applied. The surgical ophthalmic intra ocular access tool 10 can be sold in an unsterile status with warning of necessary disinfection before use, sterile in a suitably designed pack ready for use by the operator or even as a customizable 3D file ready for 3D printers. It can also be made from plastic, metal, composite(s) or any other material to suit the surgical purpose intended.

The surgical ophthalmic intra ocular access tool 10 has an oval shaped body with a space(s) in the center 28. In another embodiment, the body is round in shape, diamond or triangular. In another embodiment, the body can assume any shape to suit the purpose taking into consideration the huge variables of sizes of eyes 84 this tool may be designed for. The animal species variable alone is responsible for many embodiments, which are dictated by the application at hand.

The whole body of the surgical ophthalmic intra ocular access tool 10 is curved either permanently or can be changed manually to suit the purpose. The curvature 32 helps greatly in mimicking the shape of the outer eye wall in human eyes as well as animal eyes 84 to facilitate fixation as well as granting surgical access. The said curvature 32 can also be varied to uniquely adapt to different age group(s) including premature baby(s) needing surgery into or obtaining various fluid(s) or tissue(s) in a form including but not limited to sample(s) or biopsy(s). In other embodiments, the curvature 32 is set in such a way to specifically suit a single animal or a group of similar eyes 84 of different animals either from one or more than one species. In yet another embodiment the surgical ophthalmic intra ocular access tool 10 may be perfectly flat to suit the purpose(s) and the operator(s). The structure of the surgical ophthalmic intra ocular access tool 10 is flexible and could therefore be composed of one piece or many pieces that interlock together to form a single platform. The assembly can be in the factory in one embodiment or can be done by the operator, nurse, assistant and/or the surgeon in order to fashion the best configuration(s) for the intended purpose(s). In yet another embodiment, a removable segment of the surgical ophthalmic intra ocular access tool 10 is possible to facilitate surgical access in certain procedure(s) including but not limited to large Intra Ocular Foreign Body removal(s), ciliary body 96 resection(s) or tumors excision(s).

The surgical ophthalmic intra ocular access tool 10 size is configured in such a way along with walls 12, 14, central space(s) 28, 30 and lid-separating projection(s) 46 to keep the surgical field of the patient's eye 84 which may be human or animal of any age group exposed. The specific part of the eye 84 undergoing the surgical procedure(s) can be exposed in a specific embodiment as to enhance the surgical field required. Such intended design with meticulous exposure of the surgical field greatly increases surgeon(s) comfort and eases the whole procedure(s) and enhances surgical result(s). The same design feature can take into account the cornea 68 and/or conjunctiva 66 dryness that is a side effect of such procedures through manual, automated and/or hybrid irrigation of the surgical field(s). Thus wetting of ocular surface 84 is unaffected by non-moving lids.

The framework of the surgical ophthalmic intra ocular access tool 10 also contains wall(s) that are designed in sloping angles of fixed or variable degrees. These said wall(s) run in all 360 degrees fashion to form a structure capable of supporting different functions. These said walls also support a series of predesigned port system(s) 16 or tunnel(s) 18 that run through them. The port system(s) 16 are preplaced in specific distance(s), length(s) and angle(s) to suit the purpose(s). In other embodiment of this surgical ophthalmic intra ocular access tool 10, the port system(s) 16 run in different angle(s) in right or left side or exactly the same in one or more wall(s). In other embodiments, the tunnel(s) 18 is also preplaced on one, two, three or all four walls depending upon a specific purpose. This design is intended to produce many options suiting specific purposes for use in humans or animals eye(s) 84, which vary greatly. The entry port(s) 20 are on top of the surgical ophthalmic intra ocular access tool 10 facing the operator while the exit port(s) 22 rest on the eye wall 84. This mode of operation standardizes access each time a needle(s) 104, trocar(s), sharp and/or any blunt device(s) goes through taking medicine(s), therapeutic or diagnostic agent(s) or obtaining some form of fluid(s), tissue or tissue sample(s) or any other content for diagnostic as well as therapeutic purpose(s) in humans or animals eye(s) 84 in any age group(s). The port system(s) 16 can be as little as single in one embodiment or multiple at different distances or angle(s) or length(s) to suit the purpose of injecting into or obtaining from the eye 84 in humans or animals in any age groups(s). Fixing the port system(s) 16 to a specific angle(s), distance(s) and caliber(s) guarantees exact access every time regardless of operator skills, operator experience, patient (human or animal), eye 84 or body movement, and above all regardless of the condition(s) requiring such access. In many cases, this port system(s) 16 can provide means to release pressure from the eye to a desired level either relieving a disease or preventing high intraocular pressure (therapeutic or prophylactic). A predefined and anticipated tunnel(s) 18 can in other embodiments change along with the disease process or new advances in medicine. Such tunnel(s) 18 can be modified in form and function to keep up with newer injecting needle(s) 104 of different caliber(s) or sampling device(s) of different need(s) for different purpose(s) as well as surgical technique(s). In one embodiment, the port system(s) 16 is a straight forward opening to allow direct access when a tunnel 18 is not needed while in other embodiment(s) the tunnel 18 is angulated depending upon the surgical case(s) at hand.

In other embodiment(s), the preset port system(s) 16 have retention rim(s) 36 along the inner edge(s) to help retain inserted trocar(s) and/or cannula(s) 38. This feature allows easy fixation and/or retention of the surgical cannula(s) 38 and prevents accidental displacement which can severely endanger the surgical procedure(s) thus complication surgical task(s). Such arrangement allow for parking and/or placement cavity(s) 37 to suit the intended surgical purpose(s).

In yet another embodiment, the predefined port system(s) 16 can be equipped with magnet(s) to help attract tip(s) of metallic instrument(s) to the entry port(s) 20 easing the insertion and/or retention of said instrument(s) to the surgical field.

In a different embodiment, this entry port(s) 20 can be equipped with self-lighting landmark(s), fluorescent marker(s), magnifier(s) and/or viewing aid(s) to help the surgeon(s) find the said port(s) 20 in a darkened room and/or surgical field(s). This said aid(s) could be limited to one or all entry port(s) 20 with same or different options for each to enhance the surgical procedure(s).

This surgical ophthalmic intra ocular access tool 10 also supports a predesigned needle hub adapter(s) or receiver(s) 24 to allow complex hands-free access to the eye 84. In one embodiment, the needle hub receiver(s) 24 is designed to receive a preset needle 104 or trocar to suit the purpose while in other embodiment the needle hub receiver(s) 24 is universally suiting any form of sharp object(s) intended for the purpose(s). Yet in other embodiments, the needle hub receiver(s) 24 can be just one or multiple depending upon the intended use(s). Such said needle hub receiver(s) 24 is designed for supporting the injecting or withdrawal device(s) e.g. a syringe 100 while the plunger 102 or activating mechanism(s) is operated using single hand.

Such operation can also be automated by a machine, which may be activated via a foot pedal or even by another operator as the injecting and/or the withdrawing device(s) is fixed along with the surgical ophthalmic intra ocular access tool 10. Such design allows for complex and simultaneous surgical maneuver(s) and withdrawal procedure(s) not possible before thus expanding the scope of surgery(s). Some disease entity(s) require complex substitution of contents or filling of vacuum created by withdrawal or equalization of pressure inside the eye 84 to accomplish safe procedure(s). The entry port(s) 20 of this needle hub receiver(s) 24 is usually at the top of the surgical ophthalmic intra ocular access tool 10 facing the operator while the exit port(s) 22 at the bottom of the surgical ophthalmic intra ocular access tool 10 facing the eye 84. The exit port(s) 22 can be set at any distance(s) or angle(s) to suit the purpose(s) including but not limited to penetration depth.

All port system(s) 16 are predesigned in a fashion to allow for manual suturing of wounds if self-sealing is not adequate or upon the surgeon(s) wishes. In one embodiment, a groove to guide the suturing needle and/or the thread while in other embodiment an extra space is simply allocated for the purpose depending upon the intended surgical maneuver(s). The same arrangement(s) allows for direct observation of the wound(s) or any leak or bleeding from it.

Within the surgical ophthalmic intra ocular access tool 10 is one or more marker(s) 26 on the walls of the surgical ophthalmic intra ocular access tool 10 indicating where the surgical ophthalmic intra ocular access tool 10 should rest on the eye 84. In other embodiment, the marker(s) 26 is engraved directly on the body of the surgical ophthalmic intra ocular access tool 10. This said marker(s) 26 is well marked and can protrude from the surgical ophthalmic intra ocular access tool 10 to allow for unmistakable placement in relation to the Cornea 68-Sclera 64 junction called Limbus 70. This step is essential to safe operation of the surgical ophthalmic intra ocular access tool 10. In another embodiment, this marker 26 can only be a notch or raised area or any other shape to suit the purpose(s). The marker(s) 26 is designed in a way to facilitate view of the Limbus 70 and not to confuse the operator in any way. The marker(s) 26 can be of the same color as the rest of the surgical ophthalmic intra ocular access tool 10 and in other embodiment(s), it can be of different color, shape and/or material to the rest of the surgical ophthalmic intra ocular access tool 10. The said surgical ophthalmic intra ocular access tool 10 can contain a visual aid(s) and/or magnifier(s) to help identify and correctly place the marker(s) 26 in the intended location for safe operation.

The space in the center 28 of the body of the said surgical ophthalmic intra ocular access tool 10 has one, two or more windows, which are spread either apart or in other embodiment, connected to each other but with different locations and dimensions. In other embodiments, the central space 28 can also be round, oval, triangular, elongated or any other shape to suit the surgical task. The central space 28 can be called the anterior segment window which is designed to give access to the anterior segment of the eye 84 including but not limited to the following anatomical structures: Cornea 68, Sclera 64, Limbus 70, Iris 74, Lens 72, Ciliary body 96, anterior chamber 78 and posterior chamber of the eye 80 as well as other potential spaces between anatomic structure(s) whether in human eye or animal eye 84, in any age group(s). The access granting central space 28 is designed so that the operator can also observe changes including but not limited to extent and angle of penetration, sudden pressure changes, corneal 68 transparency, bleeding, inadvertent penetration of ocular structure(s) 84 and other anatomical changes accompanying the injecting or withdrawal procedure(s). This central space 28 also allows easy access that serves many purposes, one of which is enabling paracentesis or withdrawal of eyeball 84 contents in front of Iris 74. It also allows free form of injecting and/or withdrawal in a standalone fashion. This central space 28 may also contain a one or more predefined port system(s) 16 similar to those in the walls to a preset angle(s), depth(s) and place(s) of penetration to anterior segment of the eye 84 to suit the purpose(s). Many embodiments are possible due to great anatomical variations in humans as well as animal eyes 84 of different ages and/or species.

The marginal space(s) 30 at the surgical ophthalmic intra ocular access tool 10 can be separate from the central space 28 or connected to it in other embodiment(s). This marginal space(s) 30 can be called posterior segment window, serves many functions including but not limited to the following: providing access to normal or diseased ocular structure(s) 84 as Conjunctiva 66, Sclera 64, Ciliary body 96, Choroid 86, Retina 88, Vitreous and Vitreous cavity 82, Optic nerve 92 with vessels and any other overlying structures 94 to the above whether anatomic, pathologic, congenital or new in origin to the eye whether human eye(s) or animal eye(s) 84. This marginal space(s) 30 could be effectively used for injecting, withdrawing or altering substance(s), tissue(s), object(s), content(s), medicine(s), or sample(s) or even surface or deep biopsy of aforementioned structure(s) 84. The marginal space(s) 30 is effectively large enough for larger caliber surgical needle(s) 100 and/or trocar(s) being inserted into the eye 84 in a free form aided by the predesigned sloped wall(s) attaining a perfect angle(s) every time. In other cases if the operator wishes, by a fully manual technique, access can also be granted through this marginal space(s) 30. The operator decides when the eye 84 needs a special technique, angle or penetration depth. The same applies to newer injectors with custom needle(s) 100 and/or trocar(s) out of the usual design and/or form.

These said central space(s) 28 and/or marginal space(s) 30 also serve as reservoir(s) for containing medicine(s) necessary before, during and after the access routine. These medicine(s) can be to numb the eye 84 (anesthetic(s)), to clean (normal saline or Balanced Salt Solution (BSS)), to disinfect (Povidone-iodine or similar solution(s)) or to prevent bacterial contamination and/or infection later (Antibiotic(s)). Such design allows the intended substance(s) to stay longer effectively at the access location, increasing efficacy, decreasing frequency and preventing such fluid(s) from escaping out of effective area and into the patient cheeks. Such arrangement also decreases wiping excess fluid actions by the operator allowing more control of the procedure at hand. The same can be said for irrigating gel(s), contact solution(s) between the ocular structures 84 and any device(s) used to complement the surgical technique(s). One example being the use of sterile gel between cornea 68 and a contact lens to facilitate view into back of the eye 84.

The bottom part of the surgical ophthalmic intra ocular access tool 10 is covered with a pattern, which can be in the shape of wavy protrusion(s) designed in specific depth to stabilize the surgical ophthalmic intra ocular access tool 10 even further, preventing the eyeball 84 from moving around minimizing damage and facilitating the procedure(s). In other embodiment(s), the pattern of these projection(s) can vary in shape, size, projection height and extent to facilitate gripping to the eye tissue 84 underneath. In yet another embodiment, the underlying projection(s) can be made from the same material of the surgical ophthalmic intra ocular access tool 10 or different materials while in another embodiment, the projections can be fixed upon manufacture or assembled by the operator to suit the intended purpose(s). This said pattern also acts in a fashion to evenly distribute medicine(s), antibiotic(s), anesthetic(s) or any other fluid(s) or gel(s) in the central 28 as well as marginal space(s) 30 acting as reservoirs(s). Such design allows these substance(s) to reach port system(s) 16 entry 20 and/or exit(s) 22 maximizing their effect while containing these substance(s) for a while. In another embodiment, the whole surgical ophthalmic intra ocular access tool 10 is held in place by a suction mechanism e.g. a syringe 100 alone and/or in combination to the said pattern.

The outer wall(s) of the surgical ophthalmic intra ocular access tool 10 is designed to form an outer rail system 12 formed by a predefined groove(s) and projection(s) that outlines the outer walls of the surgical ophthalmic intra ocular access tool 10 in an interrupted or in a 360 degrees continuous fashion to allow different predesigned accessory(s) 44 to attach securely to this rail system 12. This allows many accessory(s) 44 to custom fit the outer rail 12 forming a surgical platform for the eye 84. In one embodiment, the rail 42 is formed by alternating grooves while in another an opposing curved hooks form the rail system 42, which can also be modified to fit the manufacture process(s) and the surgical purpose(s). The rail design can also vary from one segment to another or from one embodiment to another to facilitate and/or prevent cross fitting with other accessory(s). In this way, the assembly of the rail system(s)

12 & 42 is adapted to purpose(s) at hand to account for the limitless application(s) this may need to fit.

The inner wall(s) 14 of the surgical ophthalmic intra ocular access tool 10 is also designed to form a rail 42 like architecture formed by a predefined groove(s) and projection(s) that is similar or very different to those outlining the outer walls 12 and runs in an interrupted or in a 360 degrees continuous fashion to allow different predesigned accessory(s) 44 to attach securely to this rail system 42. This allows many accessory(s) 44 to custom fit the inner rail 14 forming a surgical platform for the eye 84. In one embodiment, the rail 42 is formed by alternating grooves matching the rail system 42 on the outer wall(s), while in another embodiment a different rail assembly(s) is incorporated which can also be modified to fit the manufacture process(s) and the surgical purpose(s).

The accessory(s) that attach to the inner rail 14 can vary greatly depending upon the intended purpose(s). This can include but not limited to: corneal 68 trephines of different sizes in cases of partial or total corneal 68 replacement surgery(s), centration device(s) and/or marker(s) for Toric Intra Ocular Lens(s), Multi Focal Intra Ocular Lens(s), Limbal 70 or Scleral 64 Fixation Intra Ocular Lens(s) marker(s), Intraocular telescopes implantation device(s), Limbal 70 Relaxing Incision(s) device(s), corneal 68 tunnel(s) and/or pocket(s) creating device(s), Iris 74 prosthesis device(s), light(s) holder in case(s) of corneal 68 edema, Anterior Chamber 78 Maintainer(s) (ACM) holder(s), Intra Ciliary body 96 or in-between space(s) access device(s), contact direct and/or indirect surgical lens(s) holder(s), iris 74 hook(s) and pupil 76 enlargement device(s), intraoperative ultrasound and/or Doppler scanner(s) and constant corneal 68 irrigation device(s) holder(s) and pre, intra or retro retinal 88 artificial vision device(s), electrode(s) and/or chip(s).

The accessory(s) 44 that attaches to the outer rail 12 can vary greatly depending upon the intended purpose(s). This can include but not limited to: fixed or adjustable speculum(s) 108 made of varying groove(s) 112 and projection(s) 110 proportions to suit the intended purpose(s), a micromanipulator 40 to fix, retain and/or manipulate inserted instrument(s) 60 (described in greater details later), a manual and/or an electronic micromanipulator 40 to fix, retain and/or manipulate an indenter(s) 62 (described in greater details later), keep sclerotomy(s) open in choroidal effusion(s) and/or hemorrhage(s), a light and/or laser fibers holder(s), an infusion cannula 38 holder(s) preventing accidental removal from the eye 84 causing severe ocular hypotony and compromising the surgical procedure(s), a sponge adjuster(s) to allow uniform drainage of surgical fluid(s) to the drape and/or drainage bag(s). In yet another embodiment of the speculum 108, Projection(s) 110 and accessory(s) 44 can be coated by antibacterial gel, isolating tape, drape or all of the above to prevent and/or aid in prevention of intra-ocular infections and/or endophthalmitis.

One particular accessory and/or attachment to the rail system 42 is the instrument micromanipulator 40. An essential part(s) is the jaw(s) and/or the clamp(s) 56 that holds any inserted instrument and/or object through its holding parts by pressing on its handle(s) 58. In another embodiment, a simple locking screw(s) and/or another mechanism(s) suiting the intended purpose(s) can substitute the jaws 56. This micromanipulator(s) 40 can in one embodiment be manual or electric with motor(s) in other embodiments(s). In the manual form, it can consist of one or more stages that allow full functionality(s) in form of modifying holdability of any instrument(s) 60 and/or object(s) inserted through it. The height as well as the jaw(s) 56 holding the instrument(s) 60 is fully adjustable as well as location on the surgical platform with variable tension on both. This said micromanipulator 40 can hold and/or retain, move and/or micro control any instrument(s) 60 or object(s) inserted through its jaw(s) 56. In yet another embodiment, the assembly consists of two ball heads 50 connected together by two plates 52 held by an adjustable tension screw 54. The surgeon(s) releases the tension on the plates 52 allowing the ball heads 50 to make any desired change in configuration then tightening it 54 again to retain and/or hold such specific position.

The action of the said micromanipulator(s) 40 is intended to facilitate but not limited to the following: hand-shake technique(s), Intra Ocular Foreign Body removal(s), Intra Ocular Lens exchange(s) and/or manipulation(s), very fine and/or ultra-delicate control of movement(s) allowing very controlled injection and/or aspiration of substances into very small veins, arteries, nerves 94 or between layers of the eye 84 creating potential spaces either using conventional instrument(s) 60 or very small gauge one(s) like 40G cannula(s) 38 or smaller and/or surpa-choroidal 86 and intra-choroidal 86 instrument(s) 60 guidance. This ability to electronically micro-manipulate instrument(s) 60 and/or object(s) inside the eye 84 allows for new platform of tele-surgery. The surgeon(s) is not required to attend the surgery himself but can control and/or direct some and/or all the procedure from a remote location. Another application is teaching surgery to fellows while not physically present and over the internet surgical skills demonstration(s) and/or transfer. The ability to see, ultra control instrument(s) 60 and react to tissue 84 responses is now possible through micro-controlled environment this system provides.

Viewing used can be through regular microscope, direct teleconference or even through endoscopic systems manipulated manually via another surgeon or via a remote controlled system. The surgical ophthalmic intra ocular access tool 10 can also solve the problem of automated surgical maneuvers that were not possible before including but not limited to automated pattern and/or guided laser photocoagulation and/or photography.

On yet another embodiment the surgical ophthalmic intra ocular access tool 10 works as a docking station for all instruments 60 to be used in the surgery by which each instrument 60 has its own place and can remain inside the eye 84 locked by the micromanipulator 40 until its use is needed. In the current surgical practice, it is very common to alternate between three or four instruments 60 including but not limited to the vitrector, scissors, light pipe, laser probe, diathermy and/or flute needle. Currently, each instrument 60 has to be taken out of the eye 84 to allow another instrument to be inserted even briefly while in this said embodiment the instrument 60 is simply put on hold in the micromanipulator 40 for a while until its own time comes up again. In the same setup, the surgical ophthalmic intra ocular access tool 10 can have a docked irrigating instrument 60 in addition to the usual infusion cannula 38 for automated injection of dye(s), medicine(s) or substance(s) used during the surgical procedure(s). In another embodiment, the surgical ophthalmic intra ocular access tool 10 contains a constant working instrument 60 that functions as a third hand holding and/or putting traction on the following but not limited to tissue(s), membrane(s), retina 88 or retinal 88 graft(s) or foreign body(s). This extra helping hand can in one embodiment be static, movable in steps or automated to perform vibration and/or pre-programmed micro movement(s). In yet another embodiment the said docking station can have stop-guard(s) to prevent sudden jerks, which can cause severe and/or irreparable damage. These unintentional jerks can occur due to patient movement even under anesthesia or untrained staff inside the operative room. In another embodiment, a damper is added to minimize amplitude of transmitted tremors and/or mechanical oscillations from the surgical hand to delicate tissues inside the eye.

Another particular accessory 44 and/or attachment to the rail system 42 is the indenter 62. The eyeball 84 by virtue of its shape hides important structure(s) from surgical view, which necessitates pushing, and/or indenting the outer wall inwards where the surgical instrument(s) 60 is in action within the lighted area(s) and/or surgical field(s). This indentation is done by the surgeon either him or herself causing loss of one hand functionality being occupied by holding the indenter 62 or by the nurse or an assistant. If indentation is not done by the surgeon(s) themselves, the indentation is often unsatisfactory and/or disappointing altogether. This accessory 62 attaches to the rail system 42 and provides ability(s) including but not limited to the following: to hold, control degree and/or height of indentation, control location of indentation, control shape of indenter 62 itself via switching from one shape of indenter(s) 62 to another e.g. ball ending indenter 62 vs. flat and/or broad indenter 62 and control of obliquity of indenter to match surgical path of intra-ocular instrument(s) action(s). The same accessory(s) 62 can be used to provide lighted indentation through using a light fiber and/or pipe to indent and provide illumination as two in one action. This effectively frees one surgical hand to facilitate other surgical maneuver(s). In yet another embodiment, the two elements namely the indenter 62 and the light source can be joined together as a preassembled or manually assembled by the surgeon(s). Another application is in macular 90 hole, macular 90 schisis and/or macular 90 staphyloma causing inaccessibility by the standard length surgical instrument(s) 60. The macular indenter 62 can be set then retained or adjusted depending upon the surgeon(s) wish(s). The shape of the indenter 62 can vary in different embodiment(s) to suit the surgical task(s).

In another embodiment, the surgical ophthalmic intra ocular access tool 10 can have one or more accessory(s) 44 designed to suit a specific application including but not limited to Scleral 64 Buckling surgery. In such surgery, an accessory fitting the rail system 42 can be added to do but not limited to the following: protect the cornea 68 from light and/or dryness, move or hold the eye 84, assisting with techniques assigned to a dedicated assistant, indentation(s) 62, supporting Extra Ocular Muscles like slings, helping with conjunctival 66 peritomy either limited or 360 degrees, suction of excess fluids(s), irrigation of fluid(s) needed in or outside the eye 84, making and/or keeping marker(s) in or outside the eye 84 and illuminating the operative field from within or from outside either focally or in a 360 degrees fashion.

In yet another embodiment, the surgical ophthalmic intra ocular access tool 10 is designed to suit tumor(s) treatment(s) like brachytherapy, placing and/or adjusting radioactive plaques, radiotherapy focusing and/or dose adjusting device(s) and shield(s) protecting radiation sensitive part(s) and/or organ(s). This can be combined with vitrectomy, Scleral 64 Buckling and/or tumor excision or reduction surgery(s).

In yet another embodiment, the outer and lower most part of the Surgical ophthalmic intra ocular access tool 10 contains preset and/or predesigned holes 34 and/or series of spaces 34 at lower edge(s) of said surgical ophthalmic intra ocular access tool 10 in contact with eye 84 wall(s) allowing for suturing in order to obtain secure attachment(s) or augmented wall(s) support. Such configuration simulates the purpose(s) of Flieringa ring(s) and/or McNeil Goldman Scleral and blepharostat ring(s). This will be most commonly applicable but not limited to open sky vitrectomy and case(s) requiring very large corneal 68 and/or scleral 64 incision(s) like large Intra Ocular Foreign Body removal(s), Ciliary body 96 resection(s) or tumors excision(s). In such extensive surgery(s), the eye 84 wall needs additional support that is achieved by suturing the surgical ophthalmic intra ocular access tool 10 through those said holes 34 that may be rounded, oval, elongated or any other shape to suit the surgical task(s) intended.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. A multipurpose surgical ophthalmic intraocular access tool for injecting, implanting, modifying, removing and/or obtaining: a substance, object, tissue, content, medicine, or sample from an eye, the surgical ophthalmic intraocular access tool comprising:
    a) a platform configured to be fixed or attached to the front of the eye, the platform comprising a center, an inner wall, an outer wall;
    b) at least one tunnel with an entry and exit port within the platform;
    c) at least one receiver configured to receive injection syringe, trocar or device;
    d) at least one projecting marker on at least one side of said platform configured to indicate proper placement of the platform on the eye;
    e) at least one opening at the center of the platform configured to provide access to the eye;
    f) at least one window at the center of the platform comprising a reservoir configured to retain medicine, antibiotic, anesthetic, fluid, or gel and to provide access to the eye;
    g) a set of repeated projections on an underside of the platform wherein said projections comprise a pattern configured to facilitate gripping to the eye;
    h) an outer rail comprising grooves and projections that outlines the outer wall of the platform configured to permit different accessories to attach securely to the outer rail;
    i) an inner rail that outlines the inner wall of the platform configured to permit different accessories to attach;
    j) at least one accessory that fits to at least one of the inner and outer rail wherein said at least one accessory is configured to hold, retain, control, manipulate at least one surgical instrument; and
    k) a set of holes at an edge of the platform configured for contact with the eye and receive sutures to secure the platform to the eye.

2. The tool according to claim 1, wherein the platform comprises a fixed curvature.

3. The tool according to claim 1, wherein the platform comprises a changeable curvature.

4. The tool according to claim 1, wherein the outer rail runs in a 360 degree continuous fashion around the platform.

5. The tool according to claim 1, wherein the outer rail runs in an interrupted fashion around the platform.

6. The tool according to claim 1, wherein the inner rail runs in a 360 degree continuous fashion around the platform.

7. The tool according to claim 1, wherein the inner rail runs in an interrupted fashion around the platform.

* * * * *